United States Patent
Rotem et al.

(10) Patent No.: US 8,142,400 B2
(45) Date of Patent: Mar. 27, 2012

(54) PERISTALTIC PUMP WITH BI-DIRECTIONAL PRESSURE SENSOR

(75) Inventors: Shachar Rotem, D. N. Hefer (IL); Ori Goldhor, Moshav Amikam (IL); Omer Havron, Tel Aviv (IL); Meged Offer, Netanya (IL)

(73) Assignee: Q-Core Medical Ltd., Petach Tikva (IL)

( * ) Notice: Subject to any disclaimer, the term of this patent is extended or adjusted under 35 U.S.C. 154(b) by 0 days.

(21) Appl. No.: 12/644,027

(22) Filed: Dec. 22, 2009

(65) Prior Publication Data
US 2011/0152772 A1    Jun. 23, 2011

(51) Int. Cl.
*A61M 1/00* (2006.01)

(52) U.S. Cl. ........................................ 604/153

(58) Field of Classification Search ............... 604/890.1, 604/65–67, 151, 153; 128/DIG. 12–DIG. 13
See application file for complete search history.

(56) References Cited

U.S. PATENT DOCUMENTS

| | | |
|---|---|---|
| 2,056,322 A | 10/1936 | Hoppe |
| 2,743,898 A | 5/1956 | King |
| 3,443,585 A | 5/1969 | Reinicke |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,236,880 A | 12/1980 | Archibald |
| 4,270,532 A | 6/1981 | Franetzki et al. |
| 4,320,781 A | 3/1982 | Bouvet et al. |
| 4,450,375 A | 5/1984 | Siegal |
| 4,489,863 A | 12/1984 | Horchos et al. |
| 4,682,135 A | 7/1987 | Yamakawa |
| 4,728,265 A | 3/1988 | Cannon |
| 4,741,736 A | 5/1988 | Brown |
| 4,893,991 A | 1/1990 | Heminway et al. |
| 4,978,335 A | 12/1990 | Arthur, III |
| 5,096,385 A * | 3/1992 | Georgi et al. ................... 417/18 |
| 5,103,211 A * | 4/1992 | Daoud et al. ................... 340/608 |
| 5,152,680 A | 10/1992 | Okada |
| 5,165,874 A | 11/1992 | Sancoff et al. |
| 5,213,483 A | 5/1993 | Flaherty et al. |
| 5,222,946 A | 6/1993 | Kamen |
| 5,257,978 A | 11/1993 | Haber et al. |
| 5,290,158 A | 3/1994 | Okada |

(Continued)

FOREIGN PATENT DOCUMENTS

DE    10118086 A    7/2002

(Continued)

OTHER PUBLICATIONS

U.S. Appl. No. 10/535,103 Official Action dated Feb. 2, 2009.
International Application PCT/IL2007/001398 Search Report dated Jun. 11, 2008.

(Continued)

*Primary Examiner* — Manuel Mandez
(74) *Attorney, Agent, or Firm* — Vladimir Sherman; Professional Patent Solutions

(57) ABSTRACT

Fluid delivery apparatus includes a peristaltic pump having an upstream end for receiving a fluid from a fluid source and a downstream end for delivering the fluid to a fluid target. A single pressure sensor is configured to measure, in alternation, an input pressure of the pump at the upstream end and an output pressure of the pump at the downstream end.

16 Claims, 6 Drawing Sheets

U.S. PATENT DOCUMENTS

| | | | |
|---|---|---|---|
| 5,395,320 | A | 3/1995 | Padda et al. |
| 5,429,485 | A | 7/1995 | Dodge |
| 5,499,969 | A | 3/1996 | Beuchat et al. |
| 5,509,439 | A | 4/1996 | Tantardini |
| 5,527,295 | A | 6/1996 | Wing |
| 5,575,309 | A | 11/1996 | Connell |
| 5,577,891 | A | 11/1996 | Loughnane et al. |
| 5,593,134 | A | 1/1997 | Steber et al. |
| 5,658,252 | A | 8/1997 | Johnson |
| 5,683,233 | A | 11/1997 | Moubayed et al. |
| 5,782,805 | A | 7/1998 | Meinzer et al. |
| 5,807,322 | A | 9/1998 | Lindsey et al. |
| 5,896,076 | A | 4/1999 | Van Namen |
| 5,996,964 | A | 12/1999 | Ben-Shalom |
| 6,095,189 | A | 8/2000 | Ben-Shalom |
| 6,164,921 | A * | 12/2000 | Moubayed et al. .......... 417/44.1 |
| 6,165,874 | A | 12/2000 | Powell et al. |
| 6,203,296 | B1 | 3/2001 | Ray et al. |
| 6,261,262 | B1 | 7/2001 | Briggs et al. |
| 6,339,410 | B1 | 1/2002 | Milner et al. |
| 6,371,732 | B1 | 4/2002 | Moubayed et al. |
| 6,450,773 | B1 | 9/2002 | Upton |
| 6,537,244 | B2 | 3/2003 | Paukovits et al. |
| 6,692,241 | B2 | 2/2004 | Watanabe et al. |
| 6,733,476 | B2 | 5/2004 | Christenson et al. |
| 7,018,361 | B2 | 3/2006 | Gillespie, Jr. et al. |
| 7,022,075 | B2 | 4/2006 | Grunwald et al. |
| 7,122,026 | B2 | 10/2006 | Rogers et al. |
| 7,163,385 | B2 | 1/2007 | Gharib et al. |
| 2002/0156402 | A1 | 10/2002 | Woog et al. |
| 2002/0165503 | A1 | 11/2002 | Morris et al. |
| 2003/0040700 | A1 | 2/2003 | Hickle et al. |
| 2003/0182586 | A1 | 9/2003 | Numano |
| 2004/0181314 | A1 | 9/2004 | Zaleski |
| 2004/0191112 | A1 | 9/2004 | Hill et al. |
| 2005/0088409 | A1 | 4/2005 | Van Berkel |
| 2006/0051218 | A1 | 3/2006 | Harttig |
| 2007/0269324 | A1 | 11/2007 | Goldor et al. |
| 2008/0095649 | A1 | 4/2008 | Ben-Shalom et al. |
| 2009/0221964 | A1 | 9/2009 | Rotem et al. |
| 2009/0240201 | A1 | 9/2009 | Rotem et al. |

FOREIGN PATENT DOCUMENTS

| | | |
|---|---|---|
| EP | 0215249 A1 | 3/1987 |
| EP | 0225158 A2 | 6/1987 |
| FR | 2632529 A | 12/1989 |
| JP | 60043188 A | 3/1985 |
| JP | 6-169992 A | 6/1994 |
| JP | 2002-57738 A | 2/2002 |
| JP | 2004141418 A | 5/2004 |
| WO | 9116933 A1 | 11/1991 |
| WO | 03027503 A1 | 4/2003 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |

OTHER PUBLICATIONS

International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
International Application PCT/IL2003/000947 Search Report dated Mar. 3, 2004.
Chinese Patent Application No. 200580045471.3 "Finger-type peristaltic pump" Official Action dated Jul. 18, 2008.
U.S. Appl. No. 09/125,438 Official dated Jul. 15, 1999.
U.S. Appl. No. 09/125,438 Official dated May 3, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
Rotem et al., U.S. Appl. No. 12/644,026 "Peristaltic Pump with Linear Flow Control", filed Dec. 22, 2009.
Honeywell Sensing and Control, "FSS1500NSB force sensor", Golden Valley, Minnesota, USA, 1998-2004 http://sccatalog.honeywell.com/imc/printfriendly.asp?FAM=force&PN=FSS1500NSB.
Chinese Patent Application No. 200780041966.8 Official Action dated Jul. 13, 2010.
U.S. Appl. No. 11/791,599 Official dated Aug. 19, 2010.
U.S. Appl. No. 12/514,311 Official dated Sep. 16, 2010.
U.S. Appl. No. 12/464,202 Official Action dated Oct. 3, 2011.
U.S. Appl. No. 12/463,399 Official Action dated Jul. 21, 2011.
U.S. Appl. No. 12/514,310 Official Action dated Jul. 21, 2011.
European Patent Application # 10192477.7 Search Report dated May 10, 2011.
U.S. Appl. No. 11/791,599 Official Action dated Mar. 31, 2011.

* cited by examiner

PERISTALTIC PUMP WITH BI-DIRECTIONAL PRESSURE SENSOR

FIELD OF THE INVENTION

The present invention relates generally to medical devices, and specifically to infusion pumps.

BACKGROUND OF THE INVENTION

Various types of medical infusion pumps are known in the art. One common type of infusion pump is a peristaltic pump, in which fluid is made to flow through an elastic tube by external compression of the tube. Typically, a peristaltic mechanism, such as a set of cams or fingers, compresses the tube in a cyclic pattern at a sequence of locations along the length of the tube, so as to cause the fluid to flow through the tube at a desired volumetric rate. Peristaltic infusion pumps are described, for example, in U.S. Pat. Nos. 5,290,158, 5,395,320, and 5,807,322, as well as in U.S. Patent Application Publications 2007/0269324 and 2009/0221964. The disclosures of all of these cited patents and publications are incorporated herein by reference.

SUMMARY

In many types of pumps, such as medical infusion pumps, it is desirable to measure fluid pressure both at the input to the pump and at the output from the pump. (In the context of the present patent application and in the claims, the input to the pump is referred to as the upstream end, while the output is referred to as the downstream end.) Typically, when the pump is operating, the input and output pressures are different, and two pressure sensors, at two different locations, are required in order measure the two pressures. In some embodiments of the present invention that are described hereinbelow, however, both the input and output pressure can be measured using a single sensor, thus reducing the cost and complication of the pump.

There is therefore provided, in accordance with an embodiment of the present invention, fluid delivery apparatus, including a peristaltic pump having an upstream end for receiving a fluid from a fluid source and a downstream end for delivering the fluid to a fluid target. A single pressure sensor is configured to measure, in alternation, an input pressure of the pump at the upstream end and an output pressure of the pump at the downstream end.

In some embodiments, the pump includes a flexible conduit, coupled between the upstream and downstream ends and a plurality of fingers, which are disposed at respective locations along the conduit and are configured to alternately compress and release the conduit at the locations. A pump mechanism is coupled to move the fingers between respective compressed and released positions in a cyclical pattern so as to drive the fluid through the conduit by a peristaltic action, wherein the single pressure sensor is coupled to one of the fingers.

In a disclosed embodiment, the single pressure sensor includes a force sensor, which is configured to measure the input pressure and the output pressure responsively to a force exerted on the one of the fingers while the one of the fingers is in the released position at different, respective points in the cyclical pattern. The one of the fingers may include a force relief mechanism for relieving the force on the single pressure sensor when the one of the figures is in the compressed position. In one embodiment, the one of the fingers includes a head, which engages the conduit, and the force relief mechanism includes a spring coupled between the head and the single pressure sensor.

Typically, the fingers are positioned in a row along the conduit, from a first finger at the upstream end to a last finger at the downstream end, and the single pressure sensor is coupled to a second-to-last finger in the row. In one embodiment, the plurality of the fingers consists of three fingers, and wherein the second-to-last finger is a middle finger in the row. Additionally or alternatively, the plurality of the fingers consists of four fingers, which are positioned in a row along the conduit, from a first finger at the upstream end to a fourth finger at the downstream end, and the single pressure sensor is coupled to the second or the third finger in the row.

Further alternatively, the single pressure sensor may be coupled to contact the conduit externally at a location between two of the fingers.

The peristaltic pump has a pump cycle, and the apparatus typically includes a controller, which is configured to read the input pressure and the output pressure from the single pressure sensor at respective points in the pump cycle. In a disclosed embodiment, the peristaltic pump includes a rotating shaft and a rotation sensor, which provides an output signal indicative of a position of the shaft in the pump cycle, and the controller is configured to identify the respective points in the pump cycle for reading the input pressure and the output pressure responsively to the output signal from the rotation sensor.

There is also provided, in accordance with an embodiment of the present invention, fluid delivery apparatus, including a flexible conduit, having upstream and downstream ends and a plurality of fingers, which are disposed at respective locations along the conduit and are configured to alternately compress and release the conduit at the locations. A pump mechanism is coupled to move the fingers between respective compressed and released positions in a cyclical pattern so as to drive a fluid through the conduit by a peristaltic action. A sensor is coupled to one of the fingers so as to measure a pressure of the fluid in the conduit.

There is additionally provided, in accordance with an embodiment of the present invention, a method for fluid delivery, including coupling a peristaltic pump having an upstream end and a downstream end to receive a fluid at the upstream end from a fluid source and to deliver the fluid to a patient from the downstream end. An input pressure of the pump at the upstream end and an output pressure of the pump at the downstream end are measured in alternation using a single pressure sensor.

The present invention will be more fully understood from the following detailed description of the embodiments thereof, taken together with the drawings in which:

DETAILED DESCRIPTION OF EMBODIMENTS

Figure 1:
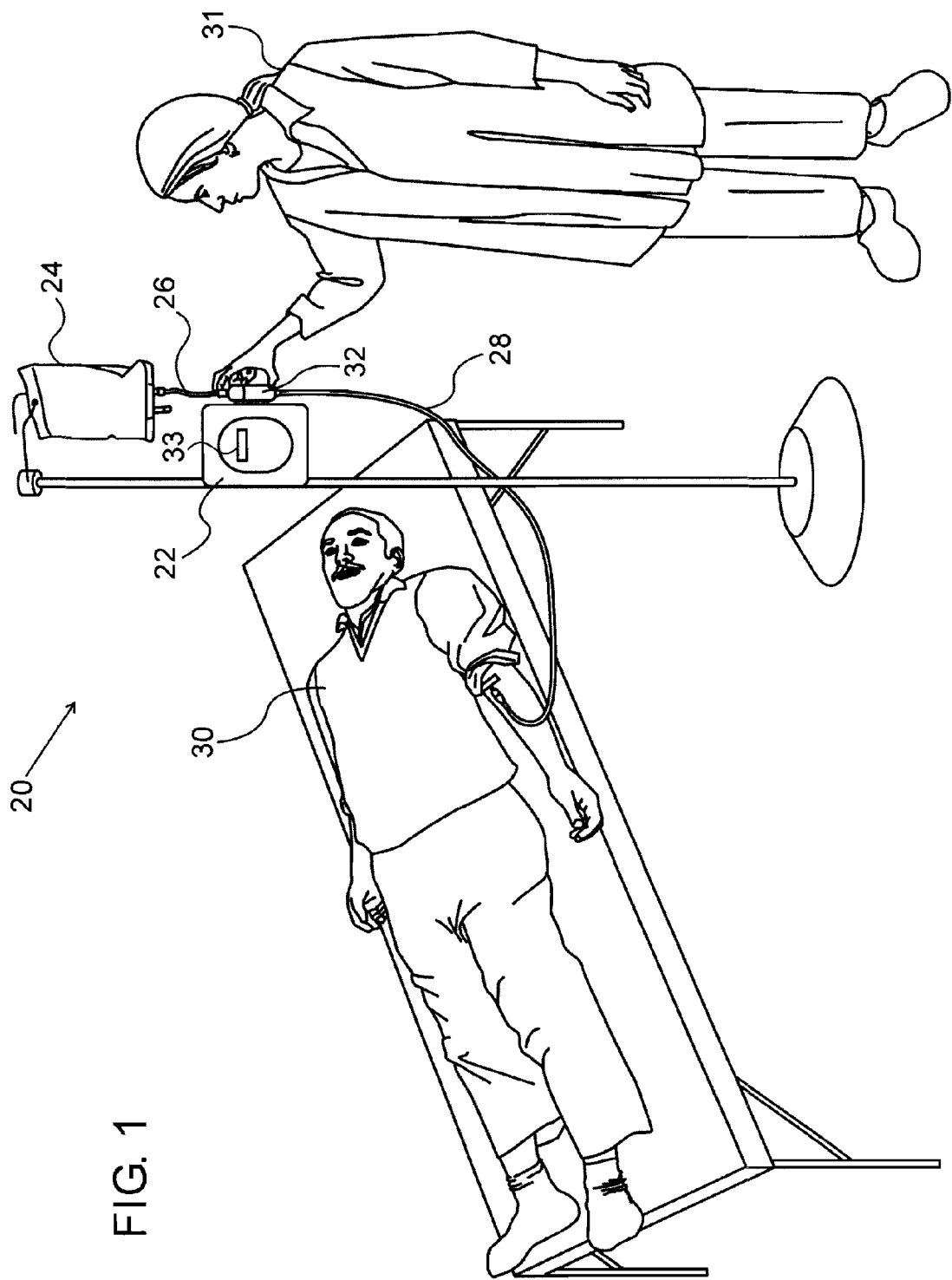
FIG. 1 is a schematic, pictorial illustration of a medical infusion system, in accordance with an embodiment of the present invention.

FIG. 1 is a schematic, pictorial illustration of a medical infusion system 20, in accordance with an embodiment of the present invention. System 20 comprises a peristaltic infusion pump 22, which pumps an infusion fluid from a fluid source, such as a reservoir 24, through an upstream tube segment 26 (commonly referred to as the "supply line") and a downstream tube segment 28 (commonly referred to as the "patient line"), to a target, which in this case is a vein of a patient 30. This particular type of infusion system is shown here by way of illustration, but the principles of the present invention, as described hereinbelow, may likewise be applied to other types of peristaltic pumps and in substantially any sort of application that uses such pumps. Although the pictured embodiment represents a clinical environment, the devices and methods described herein are also suitable for ambulatory and home use, as well as for non-medical applications.

Tube segments 26 and 28 are connected to a mechanical interface unit 32, which couples to pump 22 in a manner that is shown and explained below in greater detail. Unit 32 contains a conduit (not shown in FIG. 1) that is connected in series with tube segments 26 and 28, thus defining a flow path from reservoir 24 to patient 30. Unit 32 in this embodiment is constructed so as to enable an operator 31 to connect the unit to pump 22 stably and reliably by fitting the unit against the pump and snapping it into place. The operator sets the desired rate of fluid delivery to the patient, typically via a user interface 33 of the pump. A pump controller (as shown in the figures that follow) then regulates and monitors the operation of the pump automatically in order to deliver the desired volume of fluid safely and reliably.

Figure 2:
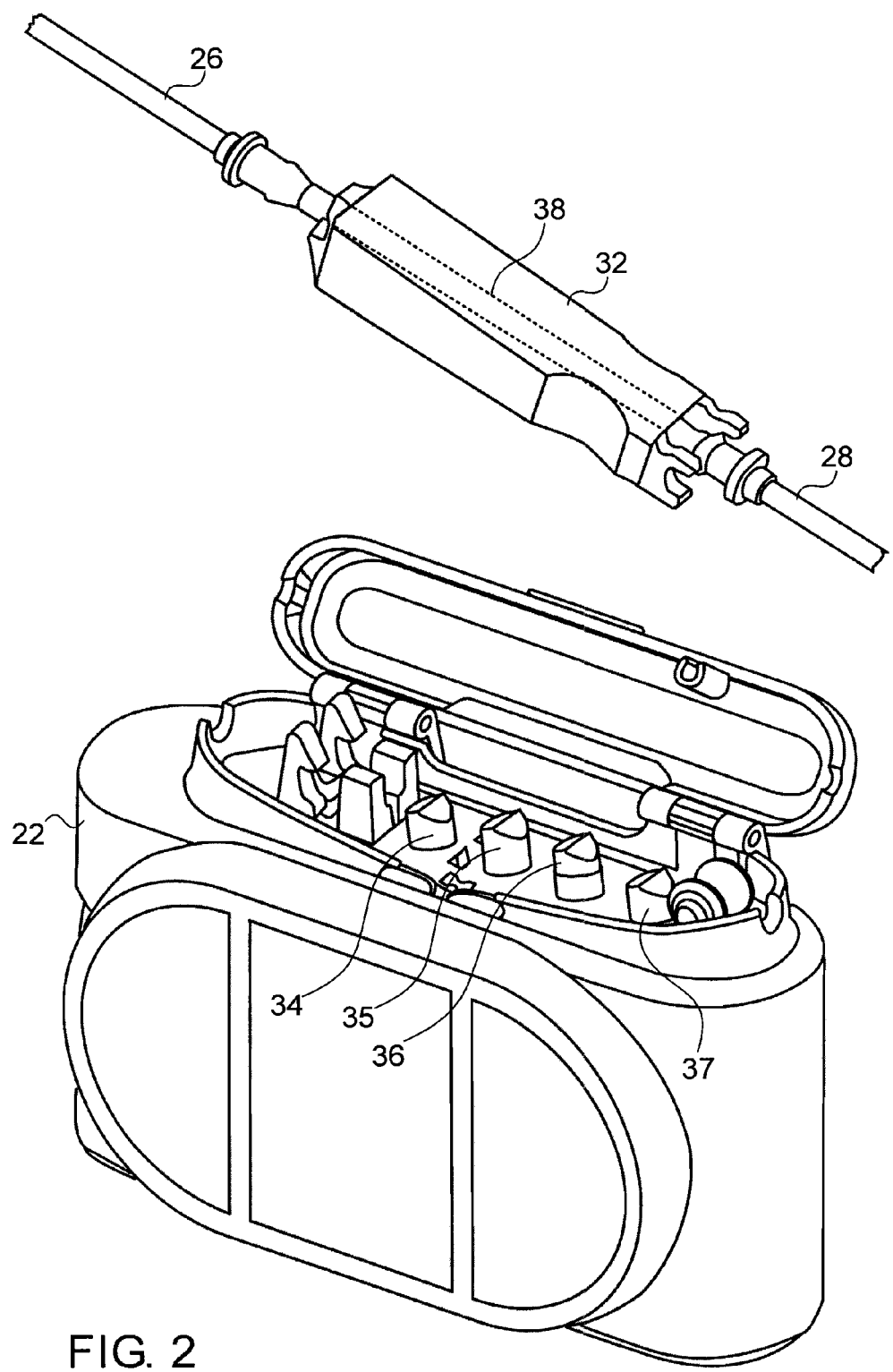
FIG. 2 is a schematic, pictorial illustration showing external details of an infusion pump, in accordance with an embodiment of the present invention.

FIG. 2 is a schematic, pictorial illustration showing external details of infusion pump 22, in accordance with an embodiment of the present invention. Mechanical interface unit 32 brings a segment of a conduit 38 into contact with a peristaltic pump mechanism comprising multiple fingers 34, 35, 36, 37 arranged in a row. Further details of mechanical interface unit 32 and its attachment to the pump are described in the above-mentioned U.S. Patent Application Publication 2009/0221964.

Conduit 38 comprises a flexible material, such as silicone. Fingers 34, 35, 36, 37 move up and down to compress and release the conduit in a predetermined cyclic pattern, so as to propel fluid downstream through conduit 38. In the pictured embodiment, the junction of conduit 38 with tube segment 26 represents the upstream end of pump 22, while the junction with tube segment 28 represents the downstream end. Equivalently, the upstream end may be identified as a point just upstream of the input of fluid to the pump mechanism, while the downstream end is a point just downstream of the output, even if there are no distinct tube junctions at these points. (For example, tube segments 26 and 28 may be produced and supplied as a single, integral tube with conduit 38.)

In medical and some other applications, it is desirable that the input and output pressure of pump 22 be measured regularly during operation. Low input pressure, for example, may indicate that the fluid in reservoir 24 has run out, whereas high output pressure may indicate that there is a blockage downstream from the pump; and both of these situations may endanger patient 30. Pump 22 may be capable of operating over a wide range of speeds, and the pressures should be measured over the entire range. It would be possible to answer these needs using two pressure sensors, one at the input and the other at the output of the pump. This solution, however, adds to the cost and complexity of the pump.

Therefore, in pump 22, a single sensor measures, in alternation, the input pressure of the pump at the upstream end of conduit 38 and an output pressure of the pump at the downstream end. For this purpose, the pressure sensor should be installed in a location where the sensor is exposed to both the input pressure and the output pressure. This objective may be achieved by placing the sensor within the pump mechanism and taking readings from the sensor at the appropriate times, in synchronization with the pump cycle. The inventors have found that a force sensor coupled to one of the intermediate fingers of pump 22, and specifically to the second-to-last finger in the row—finger 36, as shown in the figures that follow, can serve effectively as the pressure sensor for this purpose. Although the embodiment shown in the figures has four fingers, this same sensor position may be used with larger or smaller numbers of fingers, such as on the middle finger in a three-finger configuration. Alternatively, in the four-finger configuration, the force sensor may be coupled to the second finger in the row—finger 35. Further alternatively, the pressure sensor may be mounted so as to contact conduit 38 externally at a suitable location between two of the fingers, such as between the second and third fingers in the illustrated four-finger configuration.

Figure 3:
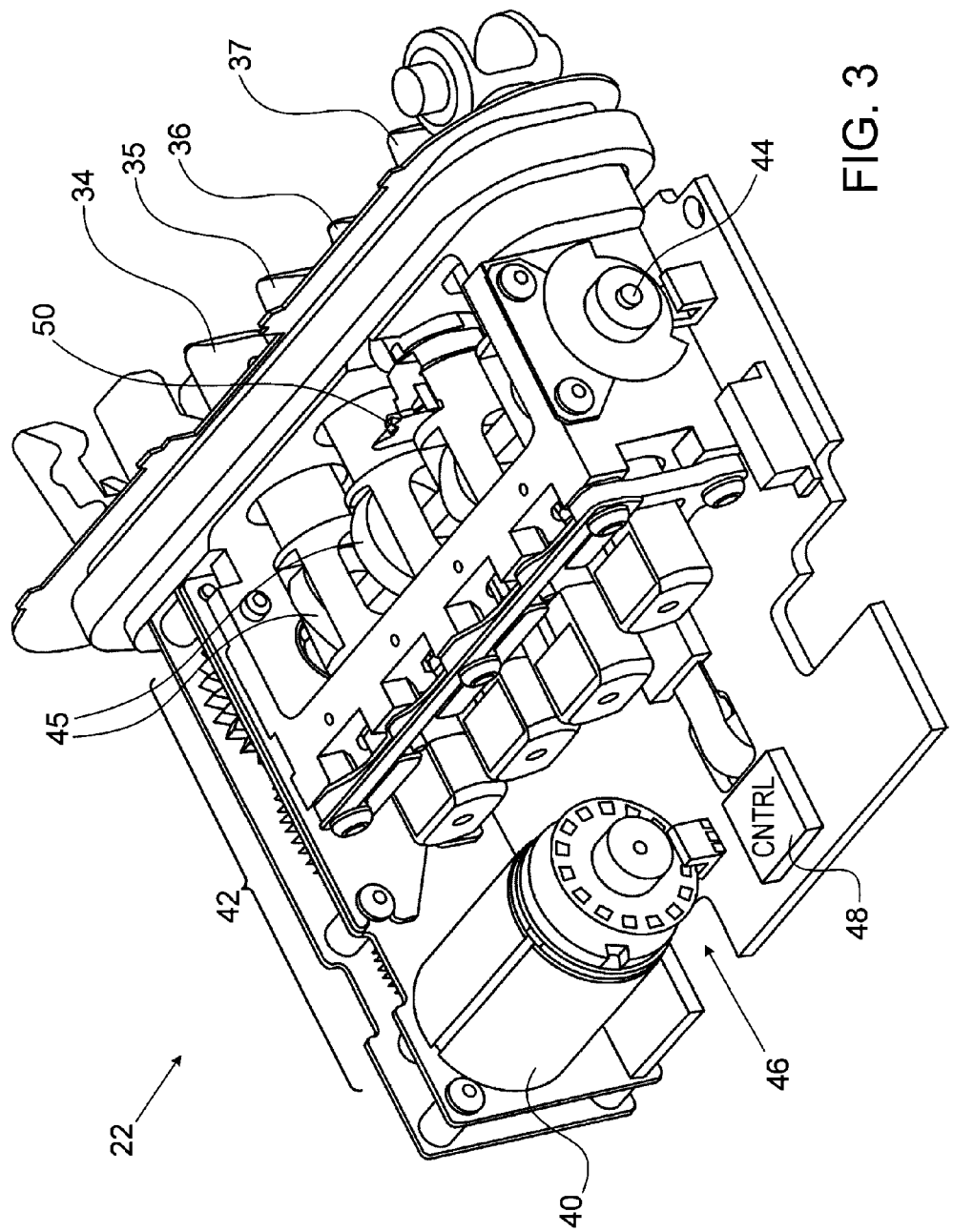
FIG. 3 is a schematic, pictorial illustration showing internal details of an infusion pump, in accordance with an embodiment of the present invention.

FIG. 3 is a schematic, pictorial illustration showing internal details of the pump mechanism in infusion pump 22, in accordance with an embodiment of the present invention. A motor 40, such as a Maxon RE-max17 DC motor (produced by Maxon Motor, Sachseln, Switzerland), drives fingers 34, 35, 36, 37 via a geared transmission 42 (such as the GX gear, also made by Maxon), which turns a camshaft 44. The camshaft turns multiple cams 45, each of which operates a respective finger 34. The phases of the cams are arranged so that the fingers alternately compress and release conduit 38 in a cyclical spatio-temporal pattern in order to move fluid through the conduit. A force sensor 50, coupled to and integrated with finger 36, measures the pressure exerted by conduit 38 on finger 36. The cyclical pattern of the fingers and the operation of the force sensor in this context are described in further detail hereinbelow.

A controller 48 drives motor 40 in order to regulate the rate of fluid flow through conduit 38. An encoder 46 measures the angle of rotation of the motor, and thus serves as a rotation sensor to provide feedback to controller 48 regarding the rotation of camshaft 44 (and hence of the rate at which fluid is pumped through conduit 38). The encoder shown in the figure is of the type comprising a wheel with windows and a light source and sensor to translate the wheel position to an electrical signal. Alternatively, any other suitable rotation sensor may be used. In the present example, there are 1308 encoder control points per camshaft rotation (based on 21.8 motor cycles to each shaft cycle and fifteen windows in the encoder wheel, wherein each window provides four location information points). Controller 48 also receives and samples signals from force sensor 50 through an analog/digital (A/D) converter (such as an 8-bit converter), in synchronization with the rotation of the camshaft, and processes these signals in order to measure the input pressure and the output pressure of pump 22 at the appropriate points in the pump cycle.

Controller 48 typically comprises an off-shelf microcontroller, such as a Microchip PIC18F8720 device (produced by Microchip Technology Inc., Chandler, Ariz.), with suitable interfaces to motor 40 and encoder 46 (and possibly to other components of pump 22, such as safety interlocks). The microcontroller is programmed in software or firmware to carry out the pressure measurement functions that are described herein. Alternatively, some or all of the functions of controller may be implemented using dedicated or programmable hardware logic circuits.

FIGS. 4A-4D are schematic side views of fingers 34, 35, 36 and 37 in pump 22, showing the cyclical spatio-temporal pattern of movement of the fingers, in accordance with an embodiment of the present invention. These figures present the state of each finger at each of the four phases of a single pump cycle. The direction of fluid flow through conduit 38, from the input to the output of the pump, is indicated by the arrows in the figures. In each phase, two of the fingers compress conduit 38 (against the interior of housing 32 in the present design), while the other two fingers are in a released position, in accordance with the positions of the respective cams. The fingers remain in positive contact with the flexible conduit even in the released position, and are thus subjected to a force exerted by the conduit that is proportional to the pressure of the fluid in the conduit.

Figure 4:
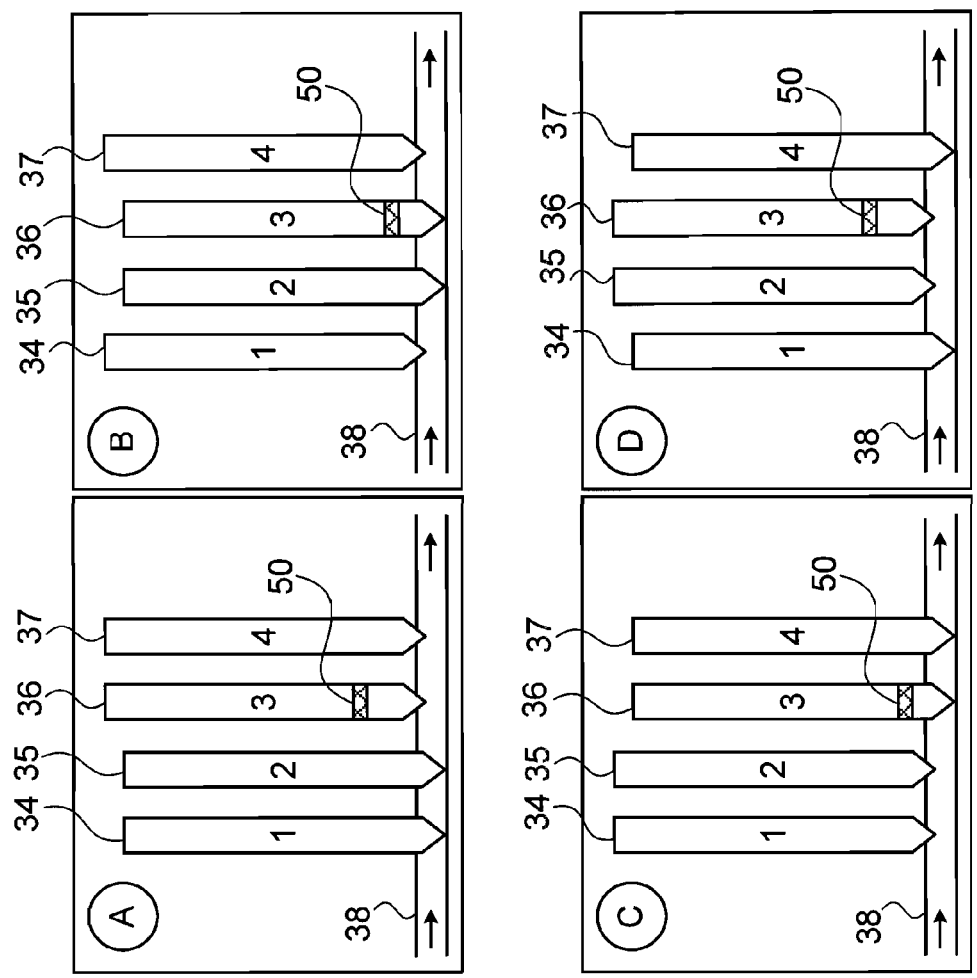
FIGS. 4A-4D are schematic side views of a set of fingers in a peristaltic assembly, showing a spatio-temporal pattern of movement of the fingers, in accordance with an embodiment of the present invention.

There are two phases in which finger 36, with sensor 50, is in the released position: the phases of FIG. 4A and FIG. 4D. In FIG. 4A, finger 36 is subject to force from the pressure of fluid flowing downstream from the pump, and thus sensor 50 in this phase measures the output pressure of the pump. Subsequently, in FIGS. 4B and 4C, the pump receives fluid from upstream, at the input pressure to the pump. In the next phase, in FIG. 4D, the received fluid, still at the input pressure, is entrapped between fingers 34 and 37, and thus sensor 50 in this phase measures the input pressure.

In FIGS. 4B and 4C, on the other hand, finger 36 is in the compressed position, so that sensor 50 is subjected to the force of the finger that presses the conduit closed, rather than the (smaller) force due to the fluid pressure. The force on the sensor in these phases could, over time, cause damage to sensor 50. Finger 36 therefore comprises a force relief mechanism for relieving the force on the sensor, as described below.

Figure 5:
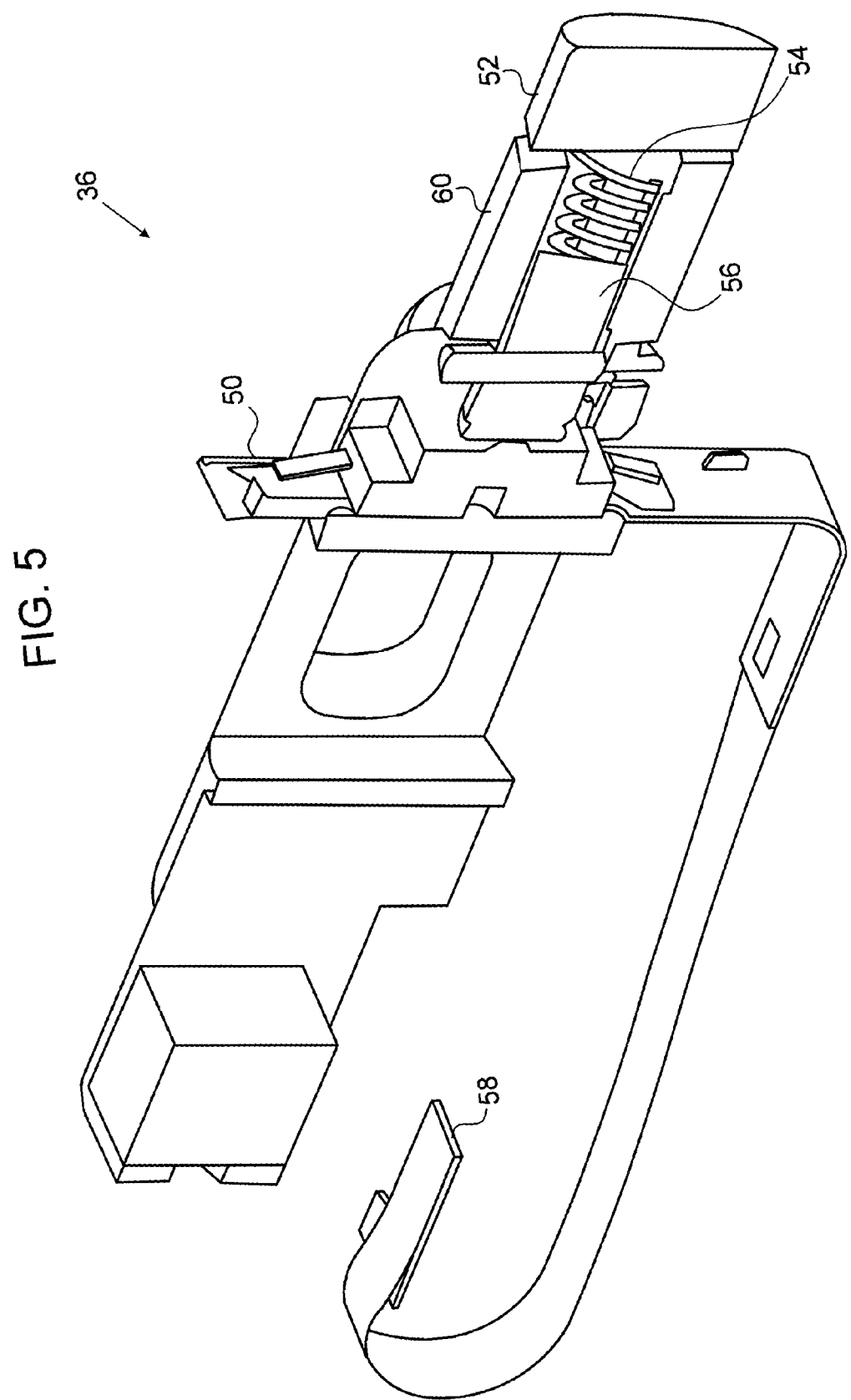
FIG. 5 is a schematic, sectional illustration of a finger in a peristaltic pump incorporating a pressure sensor in accordance with an embodiment of the present invention.

FIG. 5 is a schematic sectional view of finger 36, including sensor 50, in accordance with an embodiment of the present invention. Sensor 50 in this embodiment comprises a FSS1500NSB force sensor, produced by Honeywell Sensing and Control (Golden Valley, Minn.). The sensor outputs a signal via a connector 58 to an A/D converter in controller 48. The signal is indicative of the force exerted on a head 52 of finger 36. Alternatively, any other suitable type of force sensor that is known in the art, such as a Wheatstone bridge-based sensor, may be used in place of sensor 50.

A spring 54 couples head 52 to a base 56, which in turn presses against sensor 50. The spring and base move longitudinally within the bore of a collar 60. The spring and collar serve as the force relief mechanism, to protect the sensor from forces above a predetermined threshold. This threshold may be set, for example, to about 500 grams, by choosing a spring of the appropriate stiffness (as given by the spring constant). Below the threshold force, spring 54 is slightly compressed, but the force exerted on head 52 is still transmitted directly through the spring and base 56 to sensor 50, so that the sensor thus measures the actual force on the head. This is typically the configuration of finger 36 in the released position of FIGS. 4A and 4D. Above the threshold force, however, the spring is compressed sufficiently so that head 52 engages the shoulder of collar 60. The collar thus absorbs the force in excess of the threshold that is applied to head 52 and protects sensor 50 from damage due to the excess force.

Figure 6:
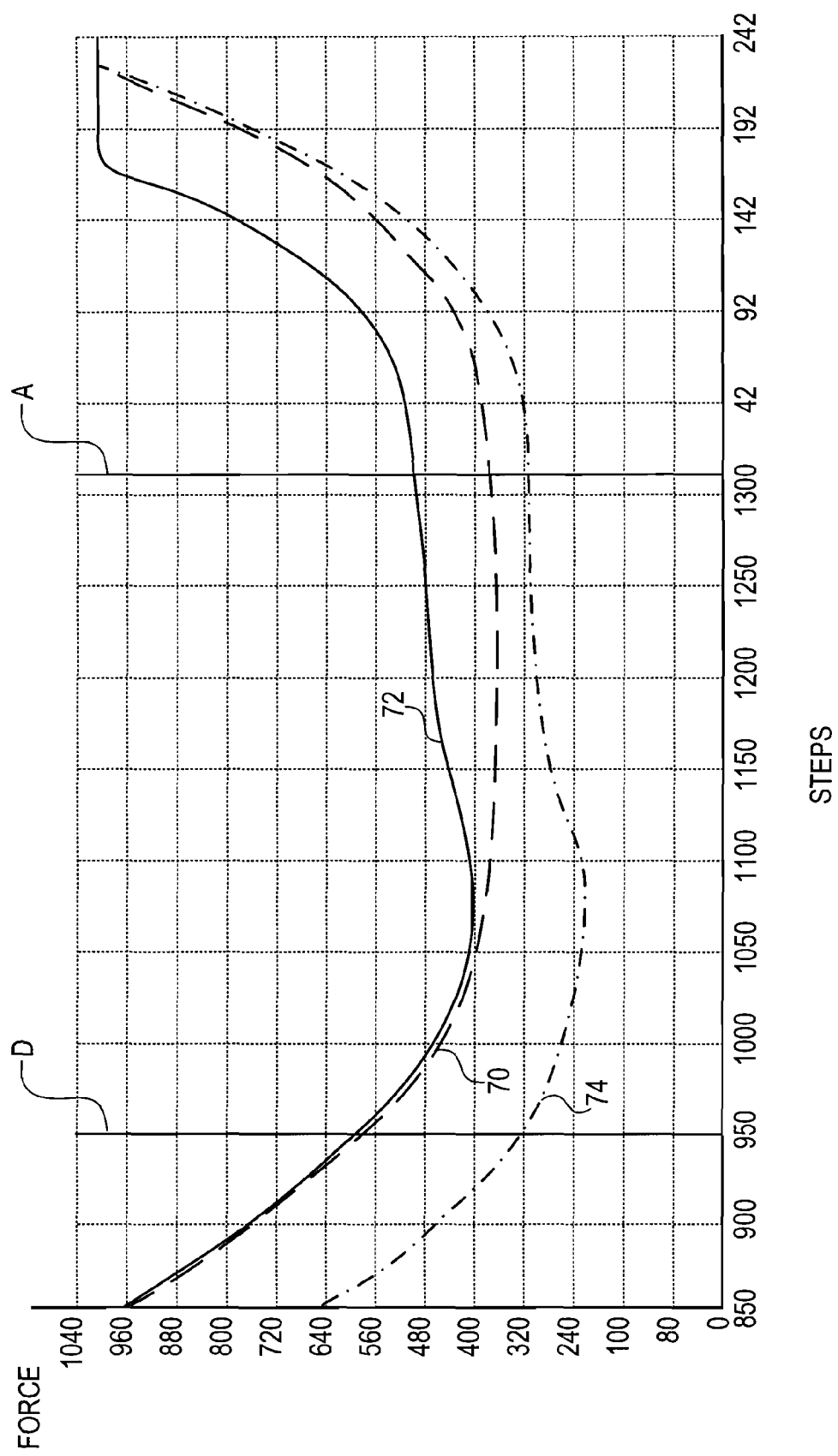
FIG. 6 is a plot that schematically illustrates pressure measurements made over the course of a pump cycle in accordance with an embodiment of the present invention.

FIG. 6 is a plot that schematically illustrates pressure measurements made by sensor 50 over the course of a cycle of pump 22, in accordance with an embodiment of the present invention. The horizontal scale in the figure is marked in steps of encoder 46 (FIG. 3). Controller 48 tracks the encoder steps and is thus programmed to identify and take force readings from sensor 50 at the appropriate points in each pump cycle. In this case, points D and A are marked in FIG. 6, corresponding to the phases shown in FIGS. 4D and 4A, for measurement of the input pressure and output pressure, respectively. The controller translates the digital force signal into the equivalent pressure value based on a conversion table, which is generated for each pump in a production calibration cycle. The calibration includes steps of creating a known pressure in the pump and reading the digital signal for these known pressure inputs. Controller 48 may display the pressure readings on user interface 33 (FIG. 1). FIG. 6 shows only a part of the pump cycle, since the phases of FIGS. 4B and 4C are not relevant to the present method of fluid pressure measurement.

A number of curves are shown in FIG. 6, corresponding to different input and output pressure conditions. A curve 70 corresponds to normal operation of pump 22, with the input pressure at point D higher than the output pressure at point A. In a curve 72, by contrast, the input pressure is normal, as in curve 70, but the output pressure at point A is elevated, indicating possible blockage downstream. In a curve 74, on the other hand, the input pressure at point D is significantly depressed, indicating that the upstream tube segment may be blocked or that the fluid reservoir is nearly empty. Upon detecting deviant pressure conditions, as in curve 72 or 74, controller 48 stops the pump operation and outputs an audible and visible alarm in order to prompt the operator to take the appropriate corrective action.

The vertical scale in FIG. 6 is marked in terms of the A/D converter range, wherein 1024 represents the full range of the digital output from sensor 50. Pump 22 is factory-calibrated, using a predefined pressure standard, as noted above, in order to program controller 48 with the appropriate voltage-to-pressure conversion parameters. A self-calibration procedure at zero output pressure is initiated in the field before pump 22 begins operation. For this purpose, for example, pump 22 is primed with fluid from reservoir 24. Since the pump output is connected to an open tube, the output pressure is zero and is set as a global reference point for the pressure measurement. This sort of self-calibration overcomes the effect that the specific conduit may have on the measurement.

Although the embodiments described above relate, for the sake of clarity, specifically to the design of pump 22, the principles of the present invention may similarly be applied in other peristaltic pumps. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Fluid delivery apparatus, comprising:
   a peristaltic pump having an upstream end for receiving a fluid from a fluid source and a downstream end for delivering the fluid to a fluid target, wherein the pump comprises:
   a flexible conduit, coupled between the upstream and downstream ends;

a plurality of fingers, which are disposed at respective locations along the conduit and are configured to alternately compress and release the conduit at the locations; and a pump mechanism, which is coupled to move the fingers between respective compressed and released positions in a cyclical pattern so as to drive the fluid through the conduit by a peristaltic action; and a single force sensor, which is coupled to one of the fingers and is configured to measure, in alternation, an input pressure of the pump at the upstream end and an output pressure of the pump at the downstream end responsively to a force exerted on the one of the fingers while the one of the fingers is in the released position at different, respective points in the cyclical pattern, wherein the one of the fingers comprises a force relief mechanism for relieving the force on the single pressure sensor when the one of the figures is in the compressed position.

2. The apparatus according to claim 1, wherein the one of the fingers comprises a head, which engages the conduit, and wherein the force relief mechanism comprises a spring coupled between the head and the single pressure sensor.

3. The apparatus according to claim 1, wherein the fingers are positioned in a row along the conduit, from a first finger at the upstream end to a last finger at the downstream end, and wherein the single pressure sensor is coupled to a second-to-last finger in the row.

4. The apparatus according to claim 3, wherein the plurality of the fingers consists of three fingers, and wherein the second-to-last finger is a middle finger in the row.

5. The apparatus according to claim 1, wherein the plurality of the fingers consists of four fingers, which are positioned in a row along the conduit, from a first finger at the upstream end to a fourth finger at the downstream end, and wherein the single pressure sensor is coupled to the second or the third finger in the row.

6. The apparatus according to claim 1, wherein the peristaltic pump has a pump cycle, and wherein the apparatus comprises a controller, which is configured to read the input and the output pressure from the single force sensor at respective points in the pump cycle.

7. The apparatus according to claim 6, wherein the peristaltic pump comprises a rotating shaft and a rotation sensor, which provides an output signal indicative of a position of the shaft in the pump cycle, and wherein the controller is configured to identify the respective points in the pump cycle for reading the input pressure and the output pressure responsively to the output signal from the rotation sensor.

8. Fluid delivery apparatus, comprising:
a flexible conduit, having upstream and downstream ends;
a plurality of fingers, which are disposed at respective locations along the conduit and are configured to alternately compress and release the conduit at the locations;
a pump mechanism, which is coupled to move the fingers between respective compressed and released positions in a cyclical pattern so as to drive a fluid through the conduit by a peristaltic action; and
a force sensor coupled to one of the fingers so as to measure a pressure of the fluid in the conduit, which is configured to measure the pressure responsively to a force exerted on the one of the fingers while the one of the fingers is in the released position at one or more specified points in the cyclical pattern, wherein the one of the fingers comprises a force relief mechanism for relieving the force on the sensor when the one of the figures is in the compressed position.

9. The apparatus according to claim 8, wherein the one of the fingers comprises a head, which engages the conduit, and wherein the force relief mechanism comprises a spring coupled between the head and the sensor.

10. A method for fluid delivery, comprising:
coupling a peristaltic pump having an upstream end and a downstream end to receive a fluid at the upstream end from a fluid source and to deliver the fluid to a patient from the downstream end, wherein the pump comprises:
a flexible conduit, coupled between the upstream and downstream ends;
a plurality of fingers, which are disposed at respective locations along the conduit and are configured to alternately compress and release the conduit at the locations; and
a pump mechanism, which is coupled to move the fingers between respective compressed and released positions in a cyclical pattern so as to drive the fluid through the conduit by a peristaltic action;
measuring an input pressure of the pump at the upstream end and an output pressure of the pump at the downstream end in alternation using a single pressure sensor by coupling the single pressure sensor to one of the fingers so as to measure a force exerted on the one of the fingers while the one of the fingers is in the released position at different, respective points in the cyclical pattern; and
relieving the force on the single pressure sensor when the one of the figures is in the compressed position.

11. The method according to claim 10, wherein the one of the fingers comprises a head, which engages the conduit, and wherein relieving the forces comprises coupling a spring coupled between the head and the single pressure sensor.

12. The method according to claim 10, wherein the fingers are positioned in a row along the conduit, from a first finger at the upstream end to a last finger at the downstream end, and wherein coupling the single pressure sensor comprises coupling the single pressure sensor to a second-to-last finger in the row.

13. The method according to claim 12, wherein the plurality of the fingers consists of three fingers, and wherein the second-to-last finger is a middle finger in the row.

14. The method according to claim 10, wherein the plurality of the fingers consists of four fingers, which are positioned in a row along the conduit, from a first finger at the upstream end to a fourth finger at the downstream end, and wherein the single pressure sensor is coupled to the second or the third finger in the row.

15. The method according to claim 10, wherein the peristaltic pump has a pump cycle, and wherein measuring the input pressure and the output pressure comprises reading the input pressure and the output pressure from the single pressure sensor at respective points in the pump cycle.

16. The method according to claim 15, wherein the peristaltic pump comprises a rotating shaft and a rotation sensor, which provides an output signal indicative of a position of the shaft in the pump cycle, and wherein reading the input pressure and the output pressure comprises identifying the respective points in the pump cycle for reading the input pressure and the output pressure responsively to the output signal from the rotation sensor.

* * * * *